United States Patent [19]

Takase

[11] Patent Number: 4,867,175

[45] Date of Patent: Sep. 19, 1989

[54] APPARATUS FOR ELECTRONIC TREATMENT USING MICROWAVES

[76] Inventor: Haruo Takase, 20-16, 3-Chome, Shimoochiai Shinjuku-ku, Tokyo, Japan

[21] Appl. No.: 198,933

[22] Filed: May 25, 1988

[30] Foreign Application Priority Data

May 28, 1987 [JP] Japan .............................. 62-82103[U]
Jan. 19, 1988 [JP] Japan .................................. 63-9253

[51] Int. Cl.⁴ .............................................. A61N 5/02
[52] U.S. Cl. .............................. 128/804; 219/10.55 F
[58] Field of Search .............................. 128/804, 399; 219/10.55 R, 10.55 F

[56] References Cited

U.S. PATENT DOCUMENTS

| | | | |
|---|---|---|---|
| 4,230,129 | 10/1980 | LeVeen | 128/804 |
| 4,316,474 | 2/1982 | Spethmann | 128/804 |
| 4,434,341 | 2/1984 | Busby | 128/804 X |
| 4,632,128 | 12/1986 | Paglione et al. | 128/804 |
| 4,747,416 | 5/1988 | Kikuchi et al. | 128/804 |

FOREIGN PATENT DOCUMENTS

| | | | |
|---|---|---|---|
| 2701934 | 7/1978 | Fed. Rep. of Germany | 128/804 |
| 3306391 | 8/1984 | Fed. Rep. of Germany | 128/804 |

*Primary Examiner*—Lee S. Cohen
*Attorney, Agent, or Firm*—Frishauf, Holtz, Goodman & Woodward

[57] ABSTRACT

A method and apparatus for treating diseases such as a malignant tumor, lesions, etc., and for killing viruses, wherein microwaves between about 6 and 15 m in wavelength are irradiated within the patient's body. The intensity and direction of irradiation are controlled to assure a safe and optimum therapeutic effect within a short period of time. The irradiation devices are preferably arranged above and below the patient, and are reciprocally movable in the longitudinal direction of the patient. The heating temperature is set within the range of 37° C. to 70° C. A timer is provided for intermittent irradiation, and a temperature sensor is provided to sense the temperature in the patient's body, and to turn off the device or sound an alarm when the temperature exceeds a predetermined value.

17 Claims, 2 Drawing Sheets

FIG_1
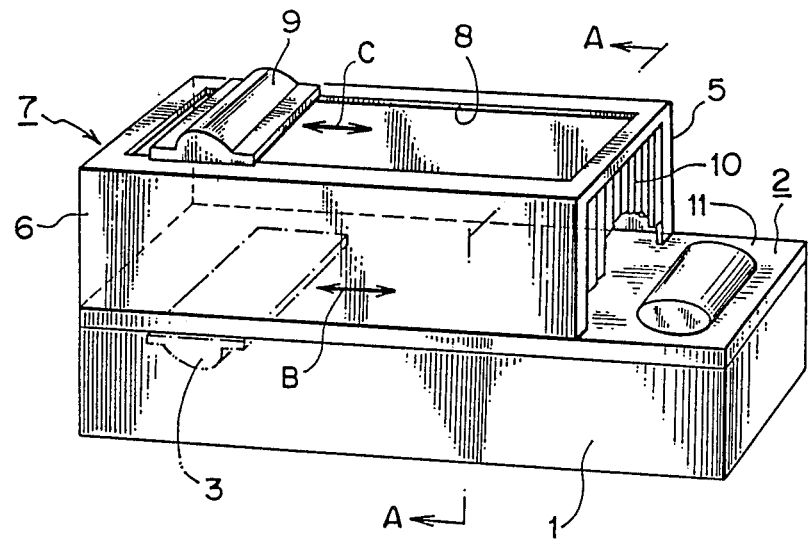
FIG_2
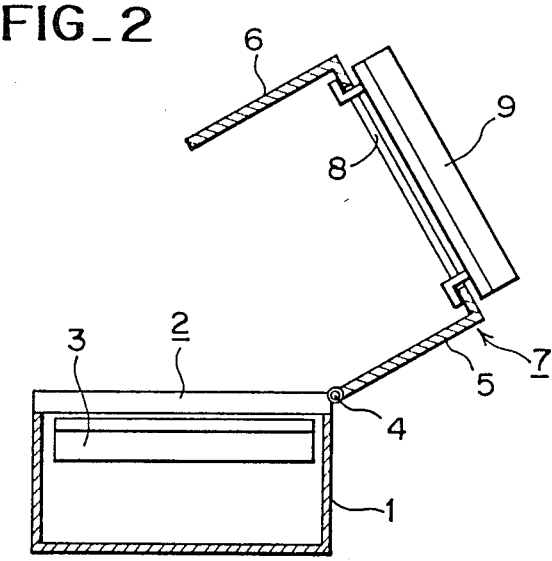

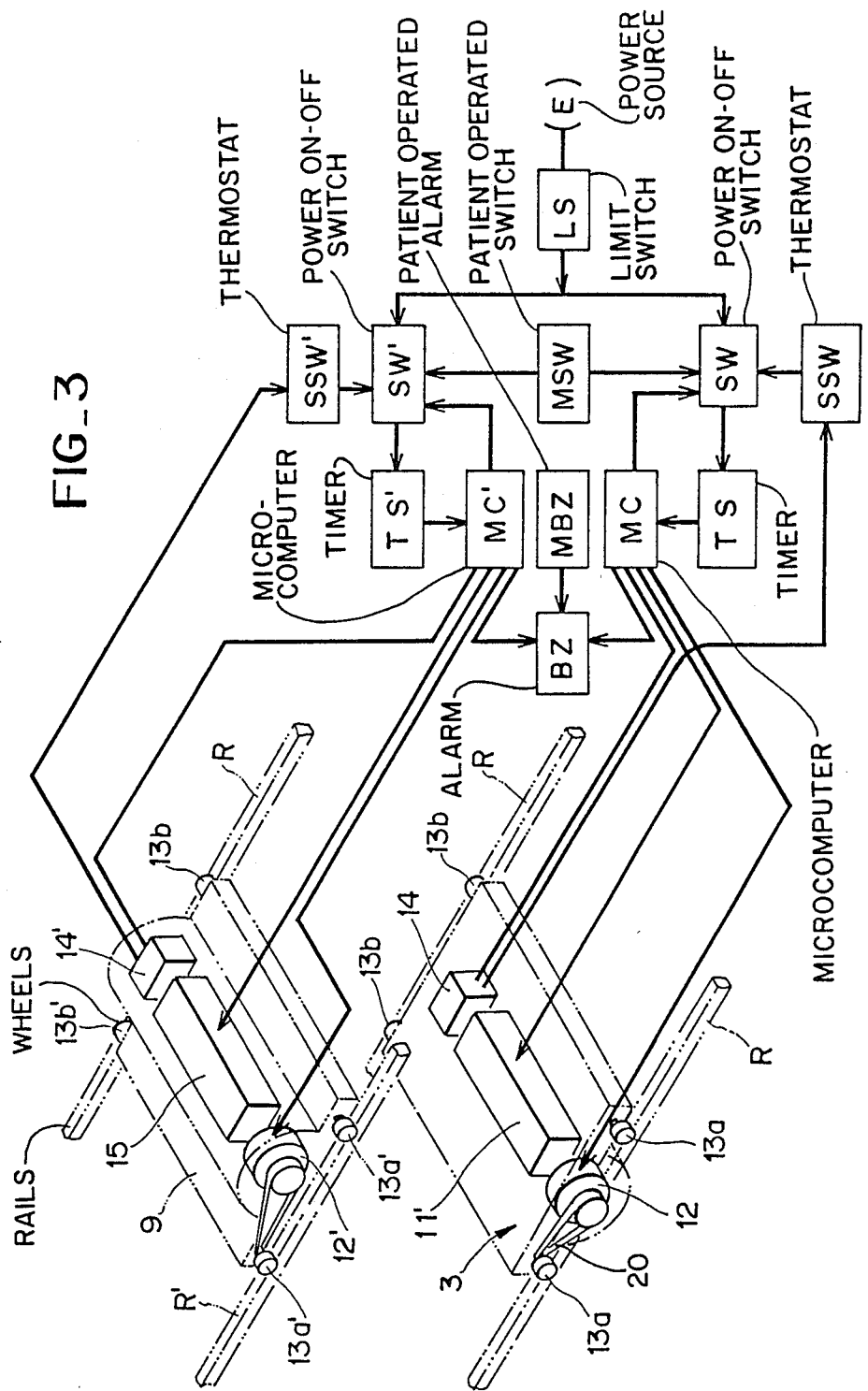

APPARATUS FOR ELECTRONIC TREATMENT USING MICROWAVES

FIELD OF THE INVENTION

The present invention relates to an electronic treatment method using microwaves and a device for carrying out the treatment, and more in particular to a method and apparatus for applying microwaves of less than 6 to 15 m to a lesion of a patient by locally heating the lesion to a predetermined temperature within a certain temperature range.

BACKGROUND OF THE INVENTION

Microwaves travel linearly, can be focused into a unidirectional beam, and can effectively heat the human body to the depth of skeletal tissues even when the patient is clothed. Therefore, applications using microwaves to treat the living body are being increasingly studied.

Many such applications, however, are still at the stage of research. Practical applications are limited to therapy of stiff shoulders and lumbagos by using microwaves for accelerating circulation and improving metabolism by utilizing the heating effect thereof.

Subsequent research on microwaves established a sure and accurate control of local heating by controlling the intensity and direction of super microwaves of 12.24 cm to thereby cause them to reach the desired tissues within the living body.

SUMMARY OF THE INVENTION

The primary object of the present invention is to provide an improved treatment method and apparatus which achieves an optimum and balanced therapeutic effect, based on the result of theoretical and clinical research, on diseases such as malignant tumors or for the destruction of various viruses, and the effects on the living body.

Another object of the invention is to provide a microwave irradiation means which can freely set the heating temperature within a predetermined range for irradiation of lesions with microwaves.

A further object of the invention is to enable fine adjustment by the patient who is being treated by permitting the patient to control the heating means for controlling the surface temperature of the body part being treated.

Still another object of the invention is to provide an apparatus and method which enables arbitrary control of the irradiation time of the microwaves.

According to the present invention, lesions or the like are treated with a microwave irradiation means mounted on a bed and which is reciprocable along the longitudinal direction of the bed. The temperature for heating the lesion by microwave irradiation is freely settable within the range of from 37° to 70° C.

BRIEF DESCRIPTION OF THE DRAWINGS

FIG. 1 is a perspective view of an electronic treatment device illustrating one embodiment of apparatus of the present invention for carrying out the method of the present invention;

FIG. 2 is a cross sectional view taken along the line A—A in FIG. 1; and

FIG. 3 schematically illustrates the system of FIGS. 1 and 2 in greater detail.

DETAILED DESCRIPTION

The present invention provides an efficient therapeutic method and means utilizing microwave irradiation to heat body portion(s) of a patient or one or more lesions on the patient's body, and eliminates the need for surgical operation.

Microwaves can be used to heat the body of a patient or a lesion in his/her body gradually to a predetermined temperature within the range of 37°–70° C. Malignant tissues or viruses are gradually destroyed and disappear after the predetermined temperature is reached, and heal the patent without damaging the body too seriously.

As for the optimum temperature to which the body portion or lesion should be heated by microwave irradiation, it is not necessarily constant as it depends on the size of the lesion, the types of malignant tumors or other diseases, the types and character of the viruses, and the condition of a patient. However, as determined by the present inventor, the temperature should be above 37° C. since it is not effective if below the natural body temperature (36.5° C.). If the temperature is above 70° C., it has been determined by the present invention that damaged and healthy living tissues may be destroyed; therefore the upper temperature limit should be set at approximately 70° C.

The present inventor has arrived at the temperature range of 37°–70° C. through experience as well as by various experiments as the most preferred range for destroying malignant tumors and other malignant cellular tissues, or for treating various viral diseases.

In order to perform rapid treatment with the temperature range of 37°–70° C. by microwaves, the present invention provides means to adjust the temperature for every 1° C. if below 40° C., in order to destroy the malignant cellular tissues and to minimize damage to the other living tissues, or to destroy viruses.

The present inventor also found it useful to provide a means whereby a patient may make fine adjustment for the temperature adjustment within the above mentioned range of 37° to 70° C. so that the patient may freely control the heating temperature to that which he feels is warm enough.

In order to ensure the safety of the microwave thermal therapy of the present invention, and to assure the patient of his safety, an alarm means is provided to emit voiced (i.e. sound) or optical alarms at predetermined temperature levels such as at 40.5° C., 55.5° C. and 60.5° C., or a thermostat means is preferably provided to automatically stop a temperature rise above the predetermined level(s). It is also effective to provide a timer mechanism for setting the microwave irradiation time arbitrarily.

Reference will now be made to the preferred embodiment of a device and method according to the present invention as shown in FIGS. 1-3 for performing the above mentioned electronic microwave treatment. As seen in FIGS. 1 and 2, a bed 2 is covered by a box shaped base 1. A protective frame or cover 7 having a cross section shaped like an inverted U is arranged above the bed 2 and is pivotally connected to base 1 along the longitudinal direction of base 1.

The bed 2 comprises a sheet-like or slab-like member 11 made of a material which allows passing of microwaves therethrough. Bed 2 is mounted to the upper part of the box shaped base 1 at an appropriate height above the bottom thereof. A microwave irradiating means 3 is mounted inside the base 1 below the bed 2, and is movable along the longitudinal direction of the bed 2 in a freely reciprocating fashion. The irradiation means 3 comprises a microwave irradiating tube 11' for irradiating microwaves upwardly toward the bed 2. This structure is shown in greater detail in FIG. 3.

As shown in FIG. 3, microwave irradiating means 3 is moved reciprocally and freely along rails R in the longitudinal direction of the bed 2 in the direction of arrow B by a known driving mechanism which is schematically shown in FIG. 3, such as an endless chain or belt 20 and motor driving means 12 for driving said chain or belt 20 via a reduction gear over two parallel rails R, R mounted on the bed 2 or base 1 along the longitudinal direction thereof. The range and speed of the reciprocal movement of microwave irradiating means 3 can be locally set by, for example, a known microcomputer MC, and a timer TS provided within the device so that continuous irradiation for certain units of time such as 1 minute, 10 minutes, 30 minutes, 1 hour, 12 hours, 24 hours or more can be performed. The system, using such a timer TS, can also be arranged so that irradiation can be stopped automatically after a predetermined time period, and/or so that irradiation can be resumed after a predetermined period of suspension.

The device is preferably further connected to a temperature sensor 14 mounted on movable irradiating means 3, for detecting the surface temperature of the patient's body or the temperature of the lesion. Also provided is an alarm means BZ or a means to automatically stop the temperature elevation beyond the prescribed upper temperature limit, so that temperatures such as 40.5° C., 55.5° C. and 60.5° C. within the above mentioned temperature range of 37° C. to 70° C. can be stored in said microcomputer MC to enable issuance of alarms when these temperatures are reached.

The alarm means BZ can be a known voiced or "sound" alarm such as a buzzer, or an optical alarm such as an alarm which lights lamps colored red or yellow according to the temperature levels.

A means for automatically suspending the temperature elevation beyond the predetermined levels can be a switch SW coupled to a thermostat SSW.

It will be further advantageous to provide a patient operated suspension switch MSW or a patient operated alarm means MBZ which a patient can manually operate when feeling ill during a therapy session or when unusual circumstances such as too hot a temperature arises.

The protective frame or cover 7 has a wide opening 8 at the top thereof, and has mounted thereon a second or upper microwave irradiation means 9 which is movable along the longitudinal direction of the frame 7 in a freely reciprocating fashion in the direction of arrow C between the left and right edge portions of said opening 8. Elements of the upper microwave irradiation means 9 which are the same as those in first-mentioned microwave irradiation means 3 are designated with the same reference numerals, but are primed and discussion thereof is omitted.

The microwave irradiation means 9 is substantially identical in construction to the microwave irradiation means 3 which runs along the lower side of the bed 2, and its reciprocable driving mechanism is also substantially identical. Radiation means 9 is provided with a microwave irradiating tube 15 extending across at least part of the opening 8, and which irradiates microwaves downwardly toward the top surface of the bed 2 as it is driven in its reciprocating movement.

The intensity of microwaves irradiated from the microwave irradiation on means 3 and 9 is dependent on their respective running speed, but it should be set within a range not to cause burns in the patient. Therefore, it is preferable to provide a sensor 14, 14' to automatically shut off the power when the intensity reaches a predetermined value which would pose dangers to the patient if exceeded and which has been selected in view of the intensity of the microwaves irradiated on the bed 2 and the running speed of the microwave irradiation means 3, 9. The sensors 14, 14' are coupled to respective thermostats SSW, SSW', which in turn are coupled to respective on-off switches SW, SW'to control power to the system.

The microwave irradiation means 3, 9 can be run in or out of synchronization with each other. They can be reciprocated over the whole length of the bed 2 or of the protective frame 7, or over a specified limited distance in order to concentrate microwave irradiation at the lesion or the like in a patient, using a control means such as known microcomputers MC, MC' as mentioned above.

In the above mentioned case, a visible ray indicator means is provided on the side of the microwave irradiation means 3, 9, or on the protective frame 7 or on the base 1, to display a visual light on the patient in a position and direction coincident with the position and direction of microwave irradiation, to thereby improve accuracy of aiming of the microwave irradiation and to improve the treatment and operational efficiency of the device.

At least the left and right side plates 5, 6 of the protective frame 7 having a cross-section, shaped like an inverted U are comprised of a shielding material which reflects and does not allow passage of microwaves. The device is further provided with a screen 10 at the front of the protective frame 7 (i.e., toward the head of a patient lying on the bed 2). The screen 10 is preferably made of a flexible microwave shielding material with vertical slits cut therein.

One side plate 5 of the protective frame 7 is mounted pivotally along one side of the bed 2 via a hinge mechanism 4 (FIG. 2). A limit switch LS (FIG. 3) is provided at an appropriate place at the base of the side plate 6 at the opposite side (not shown). When the protective frame 7 is lowered over the bed 2 and locked in place, and when the base of the side plate 6 contacts the upper surface or the side surface of the bed 2, said limit switch LS is actuated to permit start of operation of the above-mentioned microwave irradiation means 3, 9 (i.e., to close the circuit to enable providing operating power from power source E to the irradiation means 3 and/or 9).

The above-described embodiment was explained with reference to a case where the microwave irradiation means 3, 9 are moved in the longitudinal direction of the bed 2, which is fixedly mounted on the base 1. If space permits, the microwave irradiation means 3, 9 may be fixed, and the bed 2 provided with the protective frame 7 and be made movable in a reciprocating manner along the longitudinal and/or horizontal direction.

In the construction described above, the patient is made to lie down on the bed 2 with the protective frame 7 opened at the side of the side plate 6 via the hinge mechanism 4 manually (or by a not shown mechanical means) as shown in FIG. 2. After the patient lies down, the frame 7 is lowered over the bed 2. The patient is thus covered by the protective frame 7 except for his head; the patient's head is shielded by the screen 10.

The lesion or the like is confirmed by X-ray or other means with the patient thus positioned, and depending on the depth and size of the lesion, and the patient's condition, the microcomputer MC issues commands based on the pre-programmed details such as the range of reciprocal movement of the microwave irradiation means 3, 9, speed of movement of the microwave irradiation means 3, 9, the intensity and duration of microwave irradiation and the heating temperature, so that one or both of the microwave irradiation means 3, 9 is energized to start microwave irradiation of the patient lying on the bed 2, and to cause one or both of the microwave irradiation means 3, 9 to move in reciprocating movements at a constant or predetermined speed over the whole length of the bed 2 along its longitudinal direction over rails R, R', or over a prescribed length of the bed 2, limited to a localized area.

Upon completion of the treatment, the protective frame 7 is opened upward and the patient is released from the bed 2.

The construction of the present invention, as described above, achieves the following effects.

As the treatment is designed by setting the temperature for heating the lesion by microwave irradiation arbitrarily within the range of 37°-70° C., it is extremely effective for various forms of malignant tumors and other cellular or viral diseases.

The patient can be treated without taking off their clothes, since uniform heating can be obtained as deep as the skeletal tissues in the patient's body even with clothes on.

Within the temperature range of 37°-70° C., fine temperature adjustments for each 1° C. up to 40° C. and for each 0.5° C. beyond 40° C are provided, so that a speedier treatment with fine temperature control and fine adjustment for precisely destroying malignant tissues or viruses in the patient's body can be realized.

The device is provided with a switch to suspend the treatment by the patient or others by the provision of an alarm issuing means when the temperature at the lesion reaches the predetermined levels of 40.5° C., 55.5° C., and 60.5° C. within the above mentioned range of 37° C.-70° C. so that the patient can arbitrarily set the heating means adapted to his individual needs. A means to automatically stop the temperature elevation beyond the predetermined temperature is provided, and a timer mechanism to freely set the microwave irradiation hours and speed is also provided. Further provided is an alarm or emergency means to tell of any abnormality. This helps to assure the safety of the patient and achieves the same and efficient heating treatment using microwaves.

At least the right and left side plates of the protective frame 7 are made of a radio wave or microwave radiation shielding material, and a flexible screen made of a radiowave shielding material cut vertically along its vertical direction is provided at the front of the protective frame as need arises. These act to prevent leakage of the microwaves during treatment and protect the nurses and attendants attending the patient.

At the top of the protective frame 7, or at the top of the protective frame and the bottom of the bed, is provided a microwave irradiation tube directing microwave radiation toward a patient lying on the top of the bed, in a freely reciprocating manner along the longitudinal direction of the bed, to effect an efficient treatment at the optimum temperature at all times within a range not to cause localized burns in the patient. This enables providing extensive electronic treatment by heating and destroying the tissues such as malignant tumors within the patient's body, etc.

The protective frame provided with a microwave irradiation device is provided with a hinge mechanism between the lower end of one of its side plates and the base to enable the frame to be pivotally swung open upwardly above the bed, to thereby enable the patient to simply and easily climb on and off of the bed.

Various modifications and alterations can be made within the scope of the appended claims.

What is claimed is:

1. An electronic treatment device for treating at least one body portion of a patient, comprising:
    support means for supporting a patient;
    microwave irradiation means mounted adjacent said support means for emitting microwave energy toward the body of the patient, said microwave irradiation means being movable relative to said support means along at least one direction of said support means in a reciprocable fashion;
    said microwave irradiation means comprising first microwave means mounted above said support means for emitting microwave energy downwardly toward the body of the patient, and second microwave means mounted below said support means for emitting microwave energy upwardly toward the body of the patient;
    reciprocal movement imparting means coupled to at least one of said support means and said microwave irradiation means for imparting said reciprocal relative movement, and including means for independently reciprocably moving said first and second microwave means relative to said support means; and
    control means for controlling said microwave irradiation means so as to heat said at least one body portion of the patient to a treatment temperature within the range of 37° C. to 70° C. by the emitted microwave energy.

2. The electronic treatment device of claim 1, wherein said control means comprises means for controlling said microwave irradiation means to adjust the treatment temperatures in increments of about 1° C. for temperatures below 40° C., and in increments of about 0.5° C. for temperatures above 40° C., within the temperature range of 37° C. to 70° C.

3. The electronic treatment device of claim 1, further comprising patient operated adjusting means coupled to said microwave irradiation means for adjusting the heating temperature produced in the patient by said microwave irradiation means.

4. The electronic treatment device of claim 1, further comprising timer means for setting the irradiation time of microwaves from said microwave irradiation means.

5. The electronic treatment device of claim 1, further comprising sensing means for sensing the temperature in the at least one body portion of the patient being irradiated, and means coupled to said sensing means for indicating when the temperature in said body portion of the patient exceeds a predetermined value.

6. The electronic treatment device of claim 1, wherein said means for imparting said reciprocal relative movement comprises means coupled to said microwave irradiation means for reciprocably moving said microwave irradiation means relative to the patient.

7. The electronic treatment device of claim 6, wherein said moving means imparts said reciprocable movement in a longitudinal direction of the patient.

8. An electronic treatment device of claim 1, wherein said control means includes means for independently controlling said first and second microwave means.

9. The electronic treatment device of claim 1, wherein said support means includes cover means for covering the patient, said microwave irradiation means being reciprocably mounted within said cover means.

10. An electronic treatment device for treating at least one body portion of a patient, comprising:
   support means for supporting a patient;
   microwave irradiation means mounted adjacent said support means for emitting microwave energy toward the body of the patient, said microwave irradiation means being movable relative to said support means along at least one direction of said support means in a reciprocable fashion;
   said microwave irradiation means comprising first microwave means mounted above said support means for emitting microwave energy downwardly toward the body of the patient, and second microwave means mounted below said support means for emitting microwave energy upwardly toward the body of the patient;
   reciprocal movement imparting means coupled to at least one of said support means and said microwave irradiation means for imparting said reciprocal relative movement; and
   control means including means for independently controlling said first and second microwave means so as to control said microwave irradiation means so as to heat said at least one body portion of the patient to a treatment temperature within the range of 37° C. to 70° C. by the emitted microwave energy.

11. The electronic treatment device of claim 10, wherein said support means includes cover means for covering the patient, said microwave irradiation means being reciprocably mounted within said cover means.

12. The electronic treatment device of claim 10, wherein said control means comprises means for controlling said microwave irradiation means to adjust the treatment temperatures in increments of about 1° C. for temperatures below 40° C., and in increments of about 0.5° C. for temperatures above 40° C., within the temperature range of 37° C. to 70° C.

13. The electronic treatment device of claim 10, further comprising patient operated adjusting means coupled to said microwave irradiation means for adjusting the heating temperature produced in the patient by said microwave irradiation means.

14. The electronic treatment device of claim 10, further comprising timer means for setting the irradiation time of microwaves from said microwave irradiation means.

15. The electronic treatment device of claim 10, further comprising sensing means for sensing the temperature in the at least one body portion of the patient being irradiated, and means coupled to said sensing means for indicating when the temperature in said body portion of the patient exceeds a predetermined value.

16. The electronic treatment device of claim 10, wherein said means for imparting said reciprocal relative movement comprises means coupled to said microwave irradiation means for reciprocably moving said microwave irradiation means relative to the patient.

17. The electronic treatment device of claim 16, wherein said moving means imparts said reciprocable movement in a longitudinal direction of the patient.

* * * * *